(12) United States Patent
Smith et al.

(10) Patent No.: US 7,182,595 B2
(45) Date of Patent: Feb. 27, 2007

(54) DISTAL END CUTTER

(75) Inventors: Larry E. Smith, Chicago, IL (US); Andy Gurczak, Schaumburg, IL (US); Ravi P. Seeralan, Schaumburg, IL (US); Ronald J. Schindler, North Riverside, IL (US)

(73) Assignee: Hu-Friedy Mfg. Co., Inc., Chicago, IL (US)

( * ) Notice: Subject to any disclaimer, the term of this patent is extended or adjusted under 35 U.S.C. 154(b) by 0 days.

(21) Appl. No.: 10/336,623

(22) Filed: Jan. 3, 2003

(65) Prior Publication Data

US 2003/0152883 A1 Aug. 14, 2003

Related U.S. Application Data

(60) Provisional application No. 60/345,387, filed on Jan. 4, 2002.

(51) Int. Cl.
*A61C 3/00* (2006.01)
*B25F 3/00* (2006.01)

(52) U.S. Cl. .................. 433/4; 30/134; 30/124
(58) Field of Classification Search ............ 433/4; 30/124, 134, 135
See application file for complete search history.

(56) References Cited

U.S. PATENT DOCUMENTS

| | | | | |
|---|---|---|---|---|
| 2,302,810 A | * | 11/1942 | Steegmuller | 30/124 |
| 2,814,869 A | | 12/1957 | Matson | 30/124 |
| 3,456,343 A | * | 7/1969 | Breisch | 30/124 |
| 3,777,398 A | * | 12/1973 | Routh, Jr. | 30/124 |
| 3,781,993 A | * | 1/1974 | Cusato | 433/4 |
| 3,922,781 A | * | 12/1975 | Tippy | 30/124 |
| 4,035,917 A | * | 7/1977 | Roberts | 433/145 |
| 4,326,334 A | * | 4/1982 | Roux | 30/124 |
| 4,395,824 A | * | 8/1983 | Puro | 30/134 |

(Continued)

FOREIGN PATENT DOCUMENTS

DE 610644 2/1935

(Continued)

OTHER PUBLICATIONS

Notification of Transmittal of the International Search Report or the Declaration, PCT counterpart application No. PCT/US03/00110, mailed Jul. 17, 2003 of the above US application.

(Continued)

*Primary Examiner*—Ralph A. Lewis
(74) *Attorney, Agent, or Firm*—Marshall, Gerstein & Borun LLP

(57) ABSTRACT

A flush cutter of wires located on a patient's teeth has at least one pivotably carried cutting edge. An outer surface of the edge can be positioned adjacent to a surface from which the wire protrudes. An elastic insert or clamp, for griping cut wire ends, is carried adjacent to the edge. The insert has first and second spaced apart ends. A rigid surface is located to pivot toward the edge. The elastic clamp extends, in part, to the inner surface of the edge. As the cutting edge moves toward the rigid surface to cut the wire, the elastic clamp grips the cutoff wire end for removal. The rigid surface can be formed as a second cutting edge that moves toward the one cutting edge.

24 Claims, 8 Drawing Sheets

U.S. PATENT DOCUMENTS 4,627,164 A * 12/1986 Mikic et al. .................. 30/135
4,790,070 A * 12/1988 Olson .......................... 30/134
5,966,815 A * 10/1999 Sheikh ......................... 30/124

FOREIGN PATENT DOCUMENTS

DE          3802440       8/1989

OTHER PUBLICATIONS

Portion of Background of the Invention (Prior art was on sale in the United States more than 1 year before prior filing date of Jan. 4, 2002).

Figures 1 and 2 (Prior art was on sale in the United States more than 1 year before prior filing date of Jan. 4, 2002).

2 Labels for Task Flush-Cut instrument published more than 1 year before the filing date of Jan. 3, 2003 of the above-identified application.

Copies of seven views of the Task Flush-Cutter depicted as a prior art instrument in Figs. 1, 2 of the above-identified application, admitted prior art relative to the application. The seven views are labeled A-G. The instrument of Figs. 1, 2 of the present application and shown in the attached views A-G was known and used by others in this country before the date of Applicants' invention disclosed and claimed in the above-identified application.

Supplementary European Search Report, dated Feb. 24, 2006.

* cited by examiner

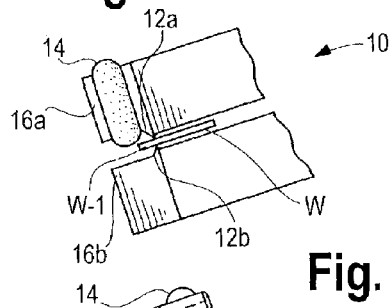
Fig. 1 PRIOR ART
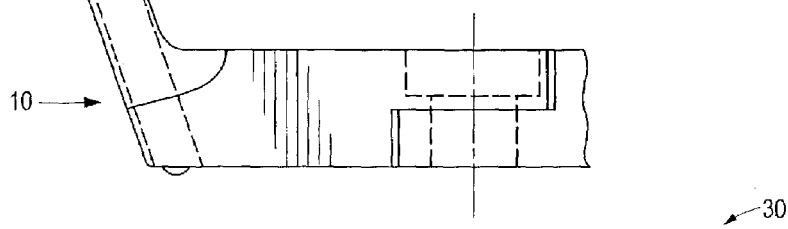
Fig. 2 PRIOR ART
Fig. 3
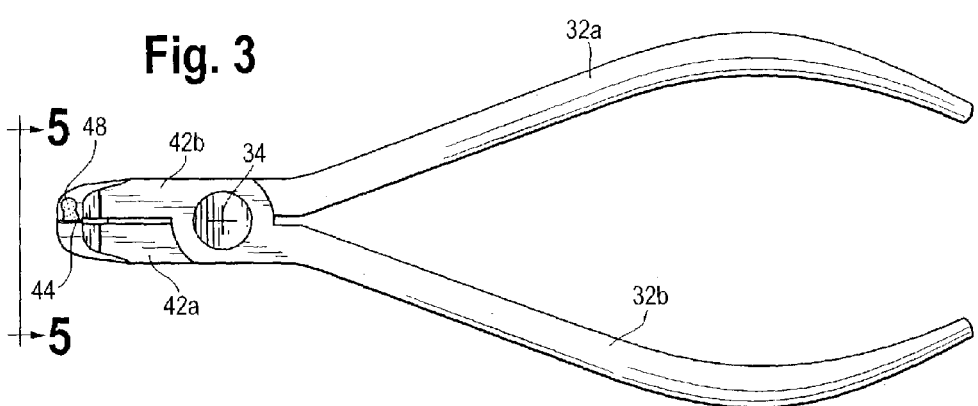
Fig. 4
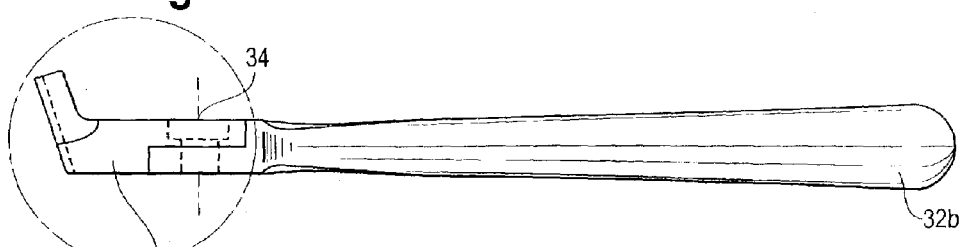
Fig. 5
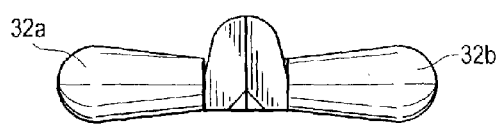

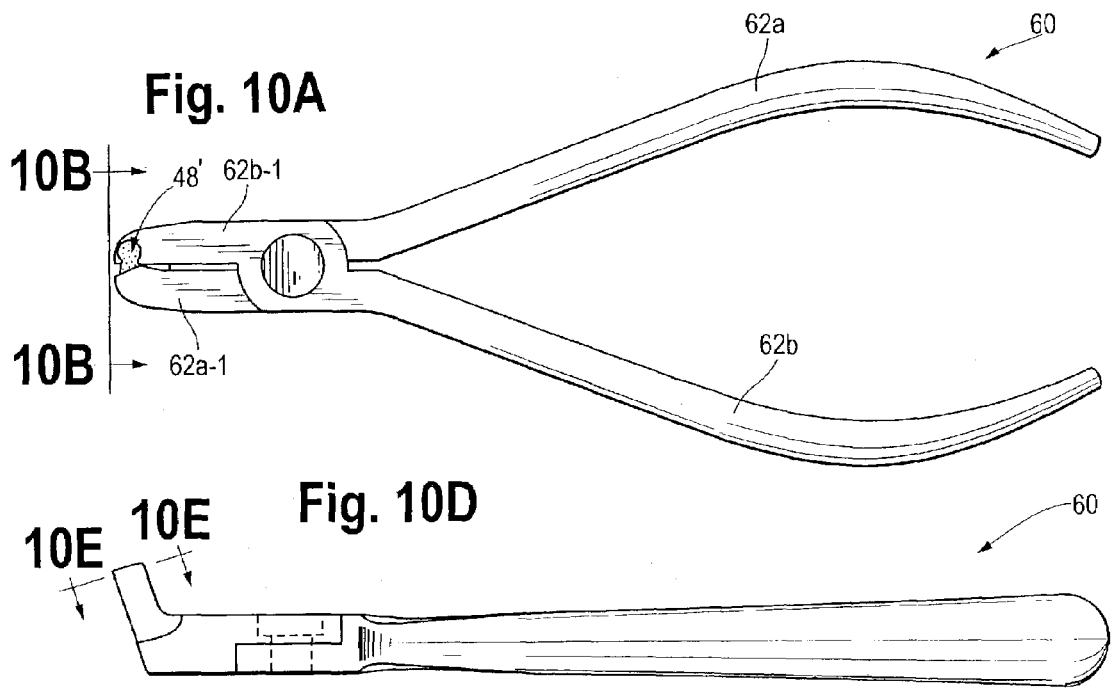
Fig. 10A
Fig. 10D
Fig. 10B
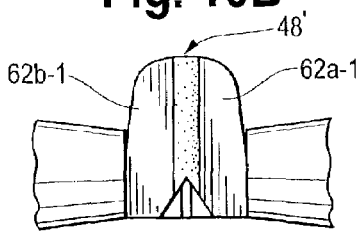
Fig. 10E
Fig. 10A-1
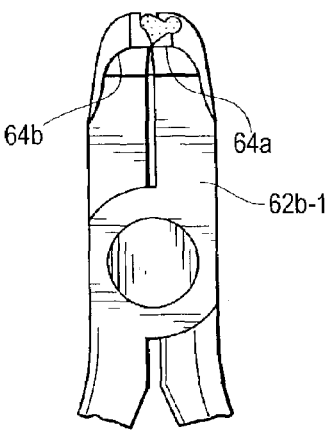
Fig. 10C

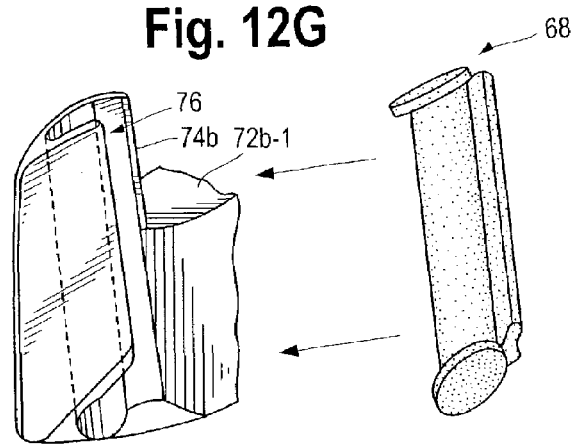
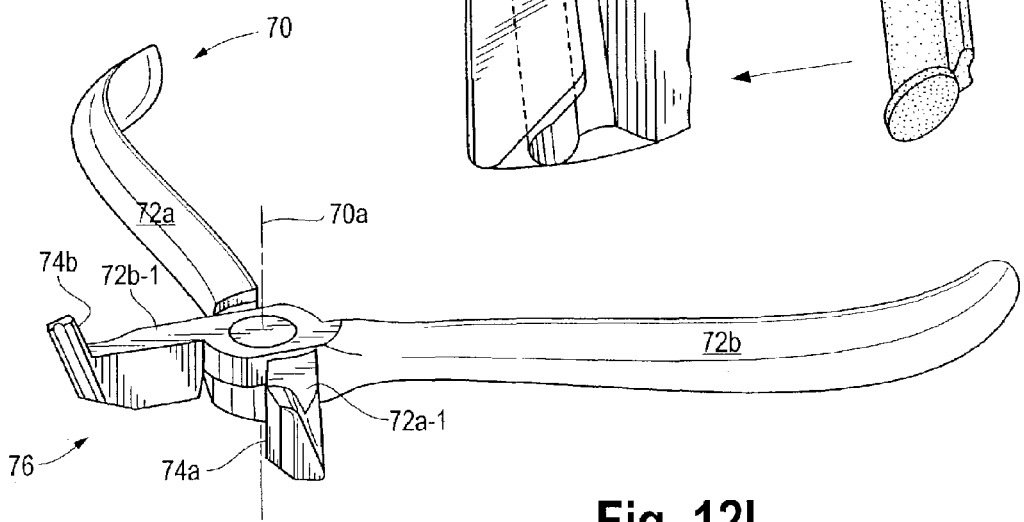
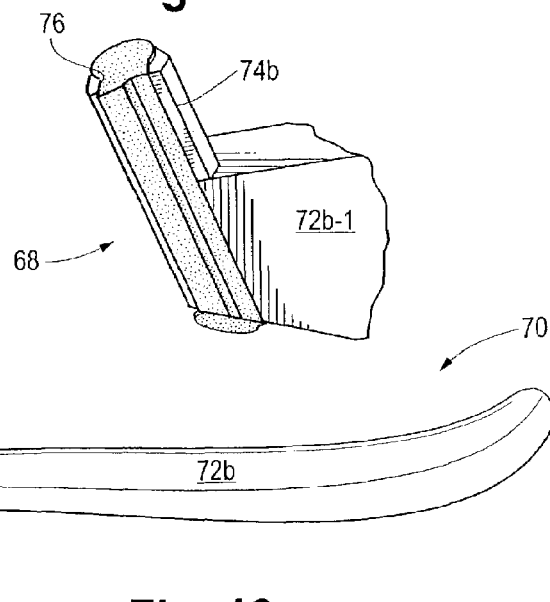
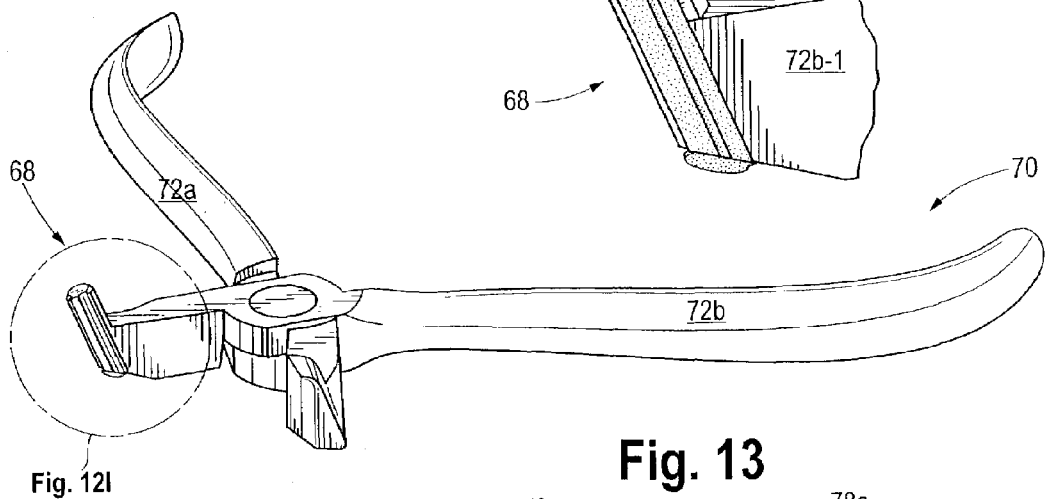
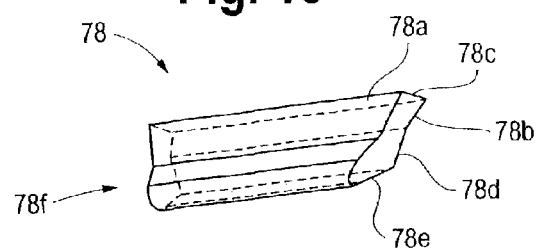

DISTAL END CUTTER

The benefit of a Jan. 4, 2002 filing date for Provisional Patent Application Ser. No. 60/345,387 is hereby claimed.

FIELD OF THE INVENTION

The invention pertains to dental instruments. More particularly, the invention pertains to wire cutters usable by orthodontists.

BACKGROUND OF THE INVENTION

In the process of adjusting location or spacing of teeth for a patient, an orthodontist will attach brackets to the respective teeth. One or more wires can be installed between brackets to enable the orthodontist to move one or more selected teeth with forces applied via the wire or wires. The ends of the wires, extending from brackets, need to be trimmed flush with the adjacent bracket(s) for patient comfort. The cut wire ends are then removed from the patient's mouth.

A known cutter employs a rubber O-ring for the purpose of gripping cut off pieces of wire. The known cutter however has limitations. When the wire length, that extends from the distal end of the bracket, dimensionally falls between the width of the cutting blades and the contact point of the O-ring, the wire can be cut, but may not be held with a desired level of certainty.

FIGS. 1, 2 illustrate the known cutter 10. The cutter 10 has first and second flush cutting edges 12a, b. An elastomeric O-ring 14 is carried by an extension 16a from cutter 12a. An extension 16b moves toward O-ring 14 as wire W is being cut. O-Ring 14 clamps cut end region W-1 against extension 16b for removal provided cut end W-1 is long enough to extend therebetween. If W-1 is too short, it will be cut but not gripped by ring 14.

There continues to be a need for orthodontic wire cutters which can reliably grip short wire ends that have been cut. Preferably, such cutters will be cost effective to manufacture and be usable at least as long as known cutters can be used.

BRIEF DESCRIPTION OF THE DRAWINGS

FIG. 1 is an enlarged fragmentary view of a known wire cutter;

FIG. 2 is a fragmentary side elevational view of the prior art cutter of FIG. 1;

FIG. 3 is a top plan view of an orthodontic cutter in accordance with the invention;

FIG. 4 is a side elevational view of the cutter of FIG. 3;

FIG. 5 is an end view of the cutter of FIG. 3;

FIGS. 10A–10E are various views of a cutter usable with the insert of FIGS. 9A, B;

FIGS. 12A–I are various views of a cutter usable with the insert of FIGS. 11A–E;

FIG. 13 is an isometric view of yet another elastomer insert;

DETAILED DESCRIPTION OF THE EMBODIMENTS

Figure 6:
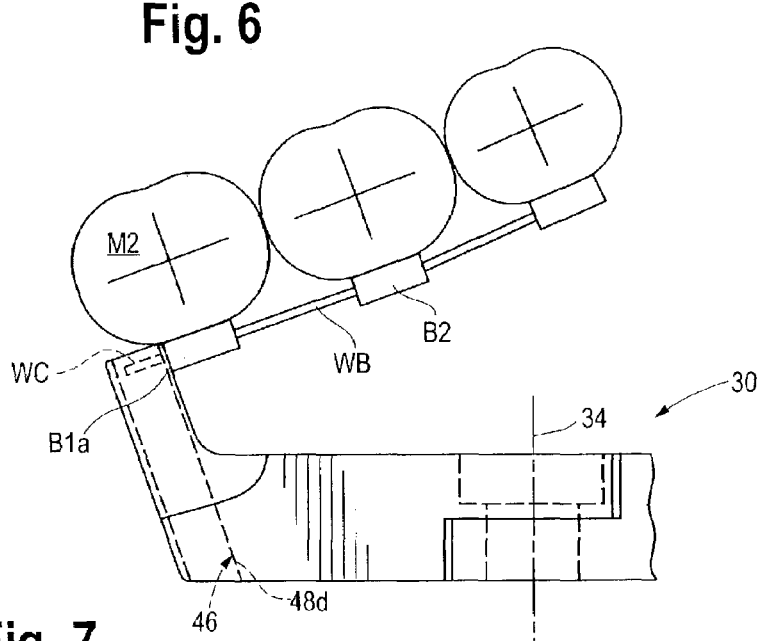
FIG. 6 illustrates exemplary wired molars with a protruding wire end to be cut with the cutter of FIG. 3.
Figure 7:
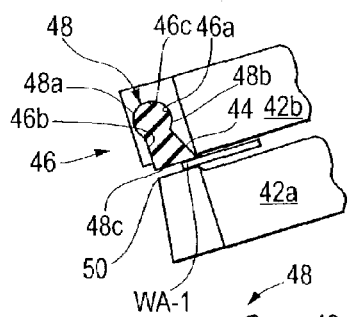
FIG. 7 is an enlarged fragmentary side view of the cutter of FIG. 3.
Figure 8:
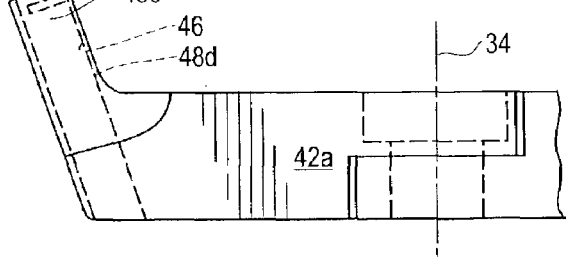
FIG. 8 is an enlarged, partial side view of the detector of FIG. 3.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

A flush cut and hold orthodontic cutter cuts orthodontic wire. When it cuts these wires, the cut portion of the wire is held within the jaws of the cutter.

The subject cutter incorporates an elastomeric, for example silicone, deformable element installed in one side of the cutter's blades. This element acts as a wire clamping device that allows the cutter's blades to be in contact with the distal surface of an orthodontic bracket during the cutting operation.

The elastomeric element is soft and pliable so that it can receive and clamp a full range of orthodontic wires reliably. The clamping portion of the element is preferably rectangular in shape so that it can grip virtually any length of wire extending from the orthodontic bracket providing it is slightly longer than the width of the cutter's blades, for example about 0.011" thick. The wire is cut flush with distal surface of the bracket usually placed on the first or second molars of an orthodontic patient.

FIGS. 2–8 illustrate details of a cutter 30 which embodies the invention. The cutter 30 can flush cut a wire end, adjacent to an orthodontic bracket, and grip the short, cut off wire end.

The cutter 30 in a disclosed embodiment, can be positioned flush against a bracket installed on a person's molar, for example. The wire end will be nipped off adjacent to the bracket by pivotally attached flush cutting edges. The cut ends will be clamped and held by an elastomeric, silicon, insert against an opposing flat surface of the cutter 30.

The insert is retained with a press-fit in an internal recess having two sides and a closed end which joins the sides. The insert can have a variety of cross sections compatible with the shape of the recess in accordance with the spirit and scope of the invention.

An end clamping region of the insert extends toward, and is preferably adjacent to the cutting edge. As the cutting edge rotates toward the wire, the end clamping region comes into contact with the wire end being cut. As the wire end is being cut from the remainder of the wire, the end clamping region, adjacent to the cutting edge, forces it against an opposing surface. The cut end is clamped between the end clamping region and the opposing surface and can be removed from the patient's mount.

The end clamping region can exhibit, for example, a rectangular or triangular cross section without limitation. Other cross sections come within the spirit and scope of the invention.

FIGS. 3–5 are various views of cutter 30. Cutter 30 has manually operable handles 32a,b which are rotatably attached at pivot 34. Jaws 42a,b extend from respective handles 32a,b and rotate toward one another as the handles 32a,b are clamped together.

One of the jaws, such as 42b carries a flush cutting edge or blade 44. An interior slot 46 is formed in the jaw 42b adjacent to the edge 44. An elastomeric member 48, described above, is retained within the slot 46.

The slot 46 is formed with two facing sides 46a,b and a closed end 46c. The elastomeric member 48, which could be formed of any medical grade elastomer, such as silicon, has first and second generally elongated sides 48a,b an elongated, exposed end clamping region or surface 48c and an elongated body length 48d.

The surface 48c can be generally rectangular. Alternately, it can be triangular. Other cross sections come within the spirit and scope of the invention. The elongated dimension 48d is at least co-extensive with an elongated dimension of the cutting edge 44.

The sides 48a, b of insert 48 have circular curved intersecting regions that join respective linear regions. The shape of the cross section facilitates removably retaining the insert 48 in the internal slot 46. Other cross sections, triangular or rectangular come within the spirit and scope of the invention.

The other jaw 42a carries a flat rigid surface 50 which extends from the edge 44 distally from pivot 34. The surface 50 also extends across end clamping surface 48c of the insert 48.

As the handles 32a,b are squeezed together, the edge 44, carried on jaw 42b and the rigid surface 50, carried on jaw 42a are clamped together to cut a wire, such as wire WA, located therebetween. At the same time, end surface 48c of the elastomeric member 48 is forced against a cut end section WA-1 of wire WA clamping same against the surface 50. The cut end of wire WA will be clamped and held between the deformable end surface 48c and rigid surface 50.

FIG. 6 illustrates one mode of use of cutter 30. As illustrated in FIG. 6, a bracket B1 has been attached to a patient's second molar M2, the rear-most molar. A Wire WB extends between at least brackets B1,2. An end WC of the wire WB protrudes from the distal end of bracket B1.

For patient comfort, it is desirable to cut off and remove the end WC. The cutting edge 44 of cutter 30 can be positioned against distal surface B1a of bracket B1. The end WC can then be cut flush against the surface B1a.

As the edge 44 cuts through the wire WB, end WC is forced by deformable end region 48c against surface 50. The deformability of the element 48 permits it to readily clamp against and retain cut wire ends of different diameters.

So long as the handles 32a,b are being squeezed together, the end WC will be retained by the cutter 30 so long as enough of it protrudes from bracket B1 to be cut by the edge 44. The presence of the elongated dimension of surface 48c adjacent to the cutting edge 44 makes it possible to grip any wire end WC protruding from cutting edge 44 toward the adjacent edge of surface 48c.

The insert 48 can be removed and replaced without any tools. The elastomeric material is not a limitation of the invention. The material can be formed into a molded or extruded insert. Preferably the elastomeric material will be bio-compatible and sterilizable, for example by autoclaving.

Figure 9A:
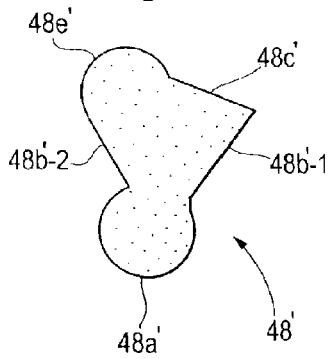
FIGS. 9A–C are various views of an alternate form of deformable insert.
Figure 9C:
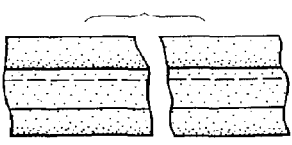
Figure 9B:
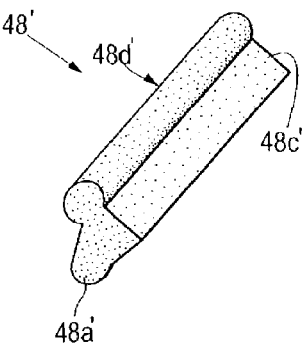
Figure 11A:
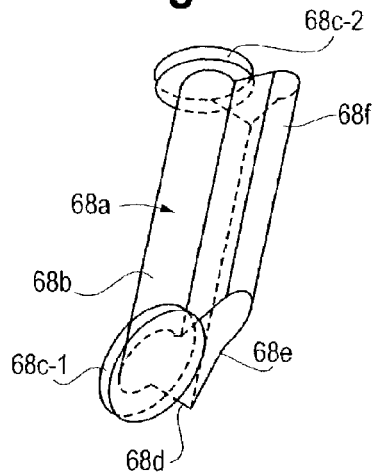
FIGS. 11A–E are various views of yet another deformable insert.
Figure 11C:
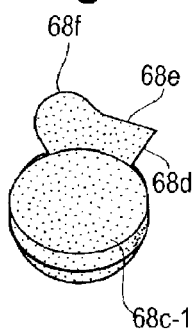
Figure 11B:
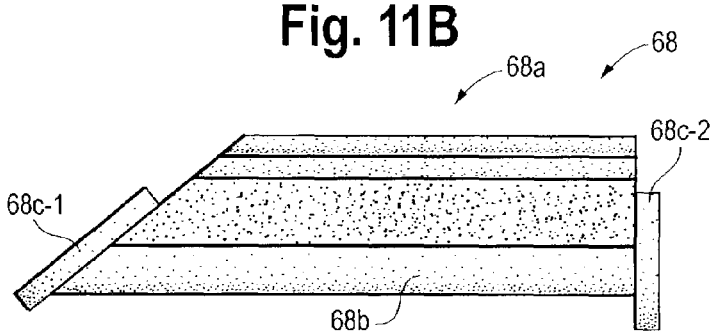
Figure 11D:
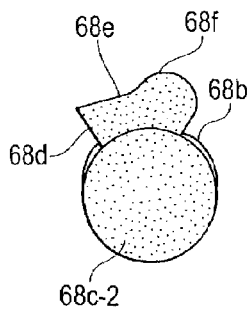
Figure 11E:
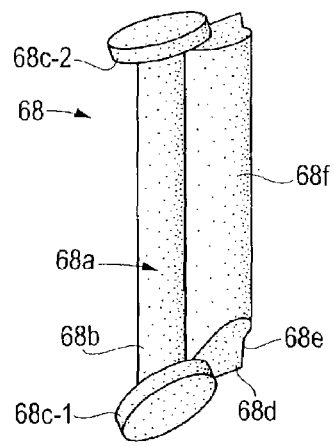

FIGS. 9A–C illustrate details of an alternate form of extruded insert 48'. The insert 48' has a curved section 48a' joined by two linear surfaces 48b'-1,-2. A planar clamping region 48c' is connected by another curved surface 48e' to the planar surface 48b'-2. The insert 48' has an elongated dimension 48d', best seen in FIG. 9B.

FIG. 9C illustrates an elastomeric extrusion 52 which has a cross section as in FIGS. 9A,B. elastomeric inserts having a length 48d' can be cut off of the extrusion 52 as needed.

FIGS. 10A–10F illustrate various views of an alternate cutter 60 which can utilize the insert 48'. Handles 62a,b carry integrally formed jaws 62a-1, b-1 which in turn carry opposed cutting edges 64a,b. The insert 48' is removably carried in an internal slot 46' which has a cross section of a shape to receive and hold surfaces 48a', b'-1 and b'-2, best seen in FIG. 10E. As the insert 48' is forced into the slot 46' it deforms slightly and returns to its nondeformed shape when fully inserted into the slot 46'. The cutter 60 can be used as described above in connection with the cutter 30.

FIGS. 11A–D illustrate details of a molded insert 68. The insert 68 has an elongated central body 68a which has a partly curved portion 68b.

The partly curved portion 60b is bounded by first and second planar, manually grippable protrusions 68c-1-2. Running axially along the curved portion 68b is a first planar section 68d which in turn joins a second planar surface or section 68e. The planar section 68e provides a deformable wire clamping surface against which a cut wire end is clamped for purposes of removing same from the mouth of the patient. The clamping surface 68e is integrally formed and is in contact with a circular surface 68f which in turn folds back to the curved body portion 68b.

Figure 12A:
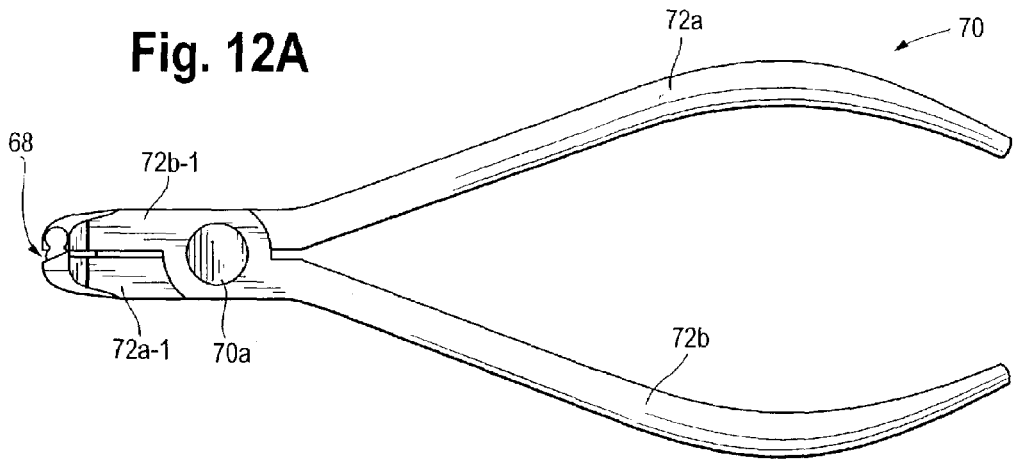

The insert 68 can be stretched for installation into an appropriate internal recess in cutters 70, best seen in FIG. 12a.

The molded insert 68 could, as those of skill in the art will understand, be formed with variations on the shape disclosed in FIGS. 11A–E without departing from the spirit and scope of the present invention. It will be understood that the exact angular arrangements of various surfaces of the insert 68 are not limitations of the present invention.

The cutter 70, illustrated in FIGS. 12A–12E, incorporates first and second handles 72a, b pivotablly attached at axis 70a. Each of the handles carries a respective jaw or extension element 72a-1, b-1. The jaws 72a-1, b-1 include first and second opposed flush cutting edges 74a, b. Flush cutting edge 74b is positioned adjacent to the insert 68, bust seen in FIG. 12A. The insert 68 is carried in an internal slot or channel 76 which extends through jaw 72b-1. The slot or channel 76 is formed with first and second sides 76a and 76b which are joined by closed end 76c. The substantially flat clamping surface 68e closes against an offset planar surface 72a-2 in jaw 72a-1.

As the handle 72a–b are clamped together, the cutting edges 74a, b cut off the distal end wire, such as wire end WC, illustrated in FIG. 6, while at the same time, the clamping surface 68e is forcing the cut wire end against rigid planar surface 72a-2 to clamp same to the cutters 70 for control and removal. As illustrated in FIG. 12A, the process of squeezing the handle 72a, b together brings the two cutting edges 74a, b as well as the flat elastomeric clamping surface 68e and the opposed rigid surface 72a-2 together abutting one another in the absence of any wire therebetween. Thus, the surface 68e has an elongated edge which is co-extensive with the cutting edges 74a, b for purposes of clamping the cut off wire end.

Figure 12B:
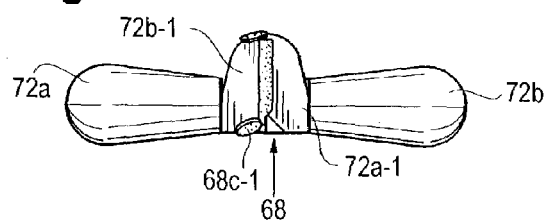
Figure 12C:
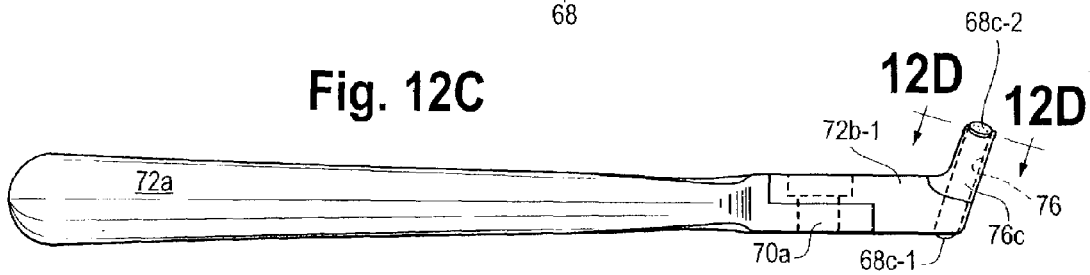
Figure 12E:
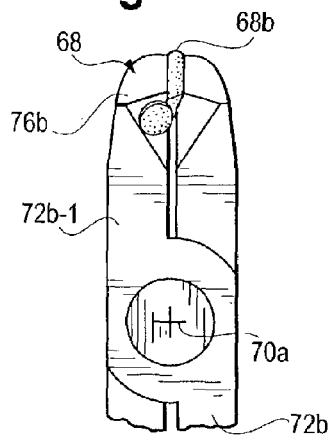
Figure 12D:
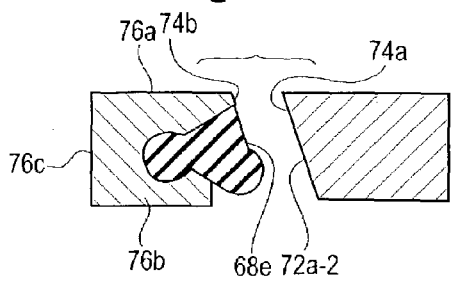

The length of the molded insert 68, as best seen in FIG. 12B, is such that the end tab 68c-1, c-2 extend on opposite sides of the respective jaws 72a-1, b-1 for installation and removal.

It will also be understood that the jaw elements 72b-1 could be formed with recesses to receive the gripping tabs 68c-1, c-2 such that those tabs could be recessed against the jaw 72b-1.

Figure 14A:
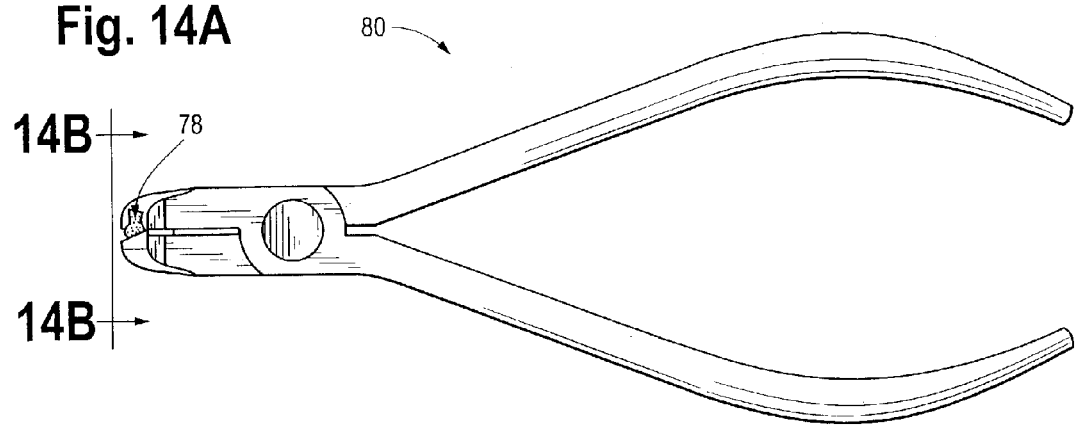
FIGS. 14A–14E illustrate various views of a flush cutter which is usable with the insert of FIG. 13.
Figure 14B:
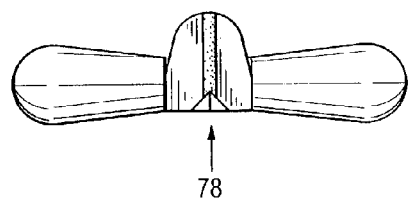
Figure 14C:
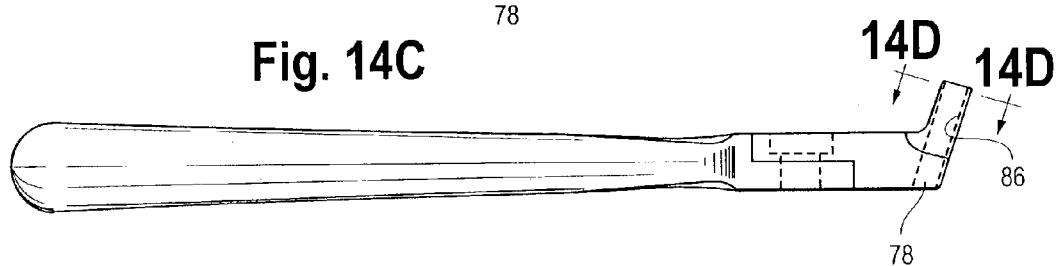
Figure 14E:
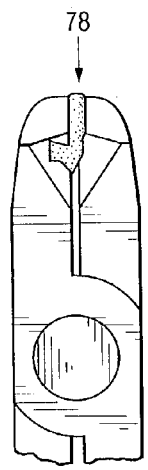
Figure 14D:
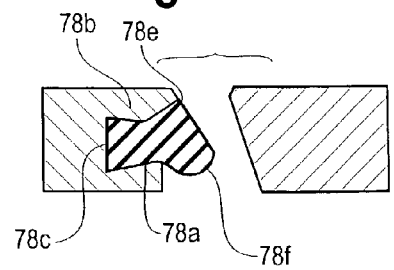

FIG. 13 illustrates another form of an elastomeric insert 78 which is formed with a substantially triangular cross section having sides 78a, b joined by end 78c. The insert 70c also includes a surface 78d which extends from side 78b to a substantially planar elongated clamping surface 78e. The surface 78e is in turn joined by a surface 78f which curves back to the side 78a. The insert 78 can be formed as an extrusion which is in turn cut to an appropriate length for insertion into cutters 80, best seen in FIGS. 14A and 14D. The insert 78 is removably received in an internal slot 86, best seen in FIG. 14C, of the cutter 80. The substantially triangular cross section of the insert 78, formed of sides 78a, b and end 78c extends along the length of the slot 86 and removably retains the insert 78 therein.

Figure 15:
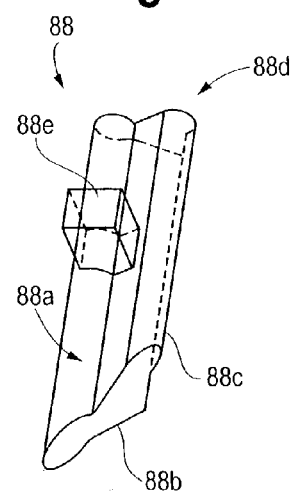
FIG. 15 is an isometric view of an alternate form of an elastomeric insert.
Figure 16A:
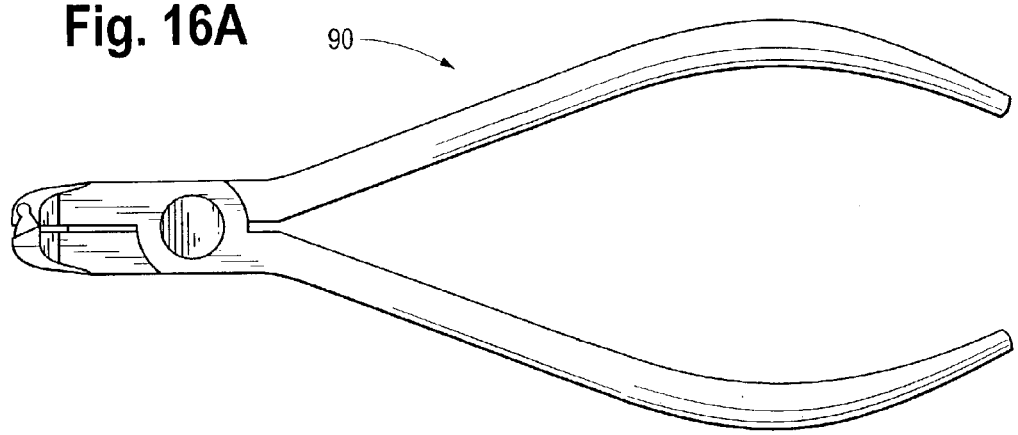
FIGS. 16A–16E are various views of a flush cutter with which the elastomeric insert of FIG. 15 can be used.
Figure 16B:
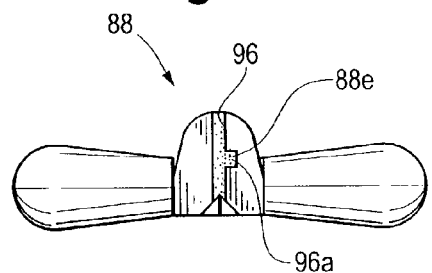
Figure 16C:
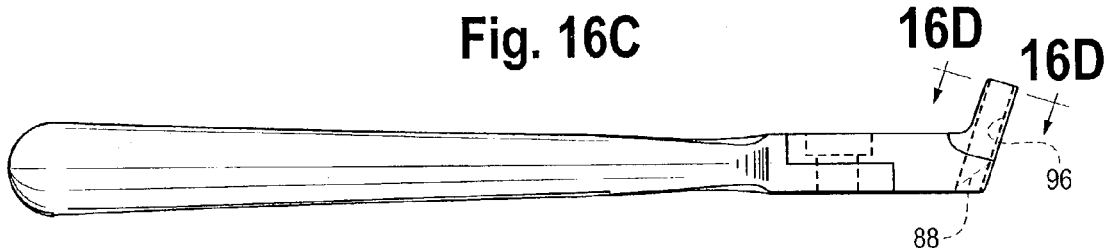
Figure 16D:
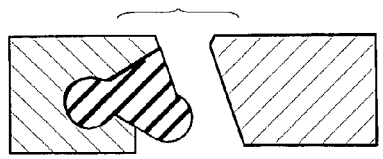
Figure 16E:
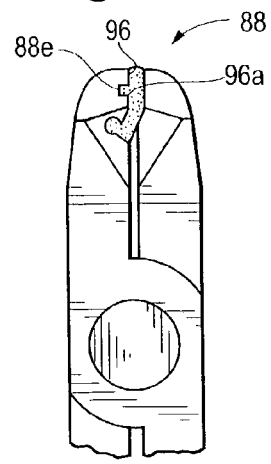

FIG. 15 illustrates the configuration of yet another elastomeric insert 88 usable with cutters 90, best seen in FIGS. 16A and 16B. The insert 88 is formed with an elongated circular end portion 88a to which is joined a planar side 88b which in turn meets planar clamping surface 88c. Surface 88d joins clamping surface 88c and folds back to the curved body portion 88a. A blocking protrusion 88e is formed on the insert 88 and is slidably received in a locking slot therefore, best seen in FIGS. 16B and E to retain insert 88 in cutters 90. Thus, the cutter 90 incorporates an internal slot or recess 96 for receipt of the body portion 88a of the insert 88 and a second slot 96a, best seen in FIG. 16B for receipt of protrusion 88e when the insert 88 is slid into position in the slot 96.

Alternate exemplary elastomeric materials for the various described inserts include ethylene propylene, ethylene propylene diene monomer, fluroelastomer, thermoplastic rubber, and flurosilicone without limitation. Preferably, hardness of the elastomeric inserts will fall in a range of 20–90 Shore A.

It will also be understood that users will be able to replace the respective elastomeric inserts when worn or otherwise in need of replacement. Such replacements can be installed without tools.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed:

1. A dental instrument for cutting and holding a wire end extending from a surface comprising:
   first and second opposed cutting edges movable relative to one another and oriented so as to be positionable against a surface from which a wire end extends;
   a separate, substantially linear, elongated elastomeric member with a gripping surface wherein the member is positioned with at least a region of the gripping surface located adjacent to one of the edges whereby as the edges move together the gripping surface of the member moves adjacent to and substantially abuts a metal part adjacent to the other edge.

2. An instrument as in claim 1 where the metal part includes a metal clamping surface, adjacent to the other edge, toward which the gripping surface moves as the cutting edges move toward one another.

3. An instrument as in claim 1 which includes first and second pivotably coupled jaws with one cutting edge carried on a respective jaw and wherein the region of the gripping surface is elongated and relatively planar.

4. An instrument as in claim 3 wherein the elastomeric member is carried in an interior recess formed on one jaw.

5. An instrument as in claim 4 wherein the other jaw carries a clamping surface toward which the planar gripping surface moves as the jaws move toward one another.

6. An instrument as in claim 5 which includes, in one of the jaws, a recess for receipt of an engaging part of the elastomeric member.

7. An instrument as in claim 3 which includes, in one of the jaws, a recess, bounded on at least three sides, for receipt of an engaging part of the elastomeric member.

8. An instrument as in claim 1 which includes,
   an extension portion with a recess for receipt of an engaging part of the elastomeric member.

9. An instrument as in claim 8 wherein the recess has a first, elongated dimension that extends from the gripping surface and has a variable width.

10. An instrument as in claim 1 where the elastomeric member is positioned in a multi-sided slot with an interference fit.

11. An instrument as in claim 1 where the elastomeric member includes at least one integrally formed insertion tab.

12. A dental instrument for cutting and holding a wire end extending from a surface comprising:
    first and second opposed cutting edges movable relative to one another and oriented so as to be positionable against a surface from which a wire end extends;
    an elongated elastomeric member with a substantially flat gripping surface where the member is positioned with at least a region of the gripping surface located adjacent to one of the edges whereby as the edges move together the region of the surface of the member moves adjacent to and substantially abuts at least part of the other edge, which includes, an extension portion with a recess for receipt of an engaging part of the elastomeric member where the recess has a first, elongated dimension that extends from the gripping surface and has a variable width wherein the variable width has second and third different dimensions to facilitate locking the elastomeric member in the recess.

13. A dental instrument for cutting and holding a wire end extending from a surface comprising:
    first and second opposed cutting edges movable relative to one another and oriented so as to be positionable against a surface from which a wire end extends;
    an elongated elastomeric member with a gripping surface where the member is positioned with at least a region of the gripping surface located adjacent to one of the edges whereby as the edges move together the region of the surface of the member moves adjacent to and substantially abuts at least part of the other edge, which includes first and second pivotably coupled jaws with one cutting edge carried on a respective jaw and where the region of the gripping surface is elongated and relatively planar, which includes, in one of the jaws, a recess, bounded on at least three sides, for receipt of an engaging part of the elastomeric member and where the elastomeric member is located substantially within the recess except for the gripping surface which extends therefrom.

14. A dental instrument for cutting and holding a wire end extending from a surface comprising:

first and second opposed cutting edges movable relative to one another and oriented so as to be positionable against a surface from which a wire end extends;

an elongated elastomeric member with a gripping surface where the member is positioned with at least a region of the gripping surface located adjacent to one of the edges whereby as the edges move together the region of the surface of the member moves adjacent to and substantially abuts at least part of the other edge, which includes a recess for receipt of an engaging part of the elastomeric member, the recess includes at least first and second non-parallel planar surfaces wherein the elastomeric member is received in the recess with a press-fit and wherein the member presents a relatively flat gripping surface adjacent to the one edge.

15. An instrument as in claim 14 wherein the elastomeric member is located substantially within the recess except for the flat gripping surface.

16. An instrument as in claim 15 wherein the flat gripping surface is substantially rectangular.

17. A dental instrument for cutting and holding a wire end extending from a surface comprising:

a flush cutting edge movable relative to an opposed rigid surface and oriented so as to be positionable against a surface from which a wire end extends;

an elastomeric member with a substantially flat gripping surface wherein the member is positioned with at least a region of the flat gripping surface located adjacent to one of the edge or the opposed surface, whereby as the edge moves toward the opposed surface, the region of the flat surface also moves, the elastomeric member is received in a recess with a press-fit and presents a relatively flat gripping surface adjacent to the one of the edge or the opposed surface.

18. An instrument as in claim 17 wherein the elastomeric member is located substantially within the recess except for the flat gripping surface.

19. An instrument as in claim 18 wherein the flat gripping surface is one of substantially rectangular or substantially triangular.

20. An orthodontic cutter comprising:
at least one flush cutting edge;
an interior recess formed adjacent to the edge; and
a removable and replaceable, deformable, substantially linear, wire clamping member substantially carried in the recess, the member having first and second displaced ends, the ends having substantially the same cross section.

21. A cutter as in claim 20 wherein the recess is elongated with a closed end and a displaced open end.

22. A cutter as in claim 21 wherein the recess has a variable width parameter.

23. A cutter as in claim 20 which includes a second flush cutting edge in opposed relation to the flush cutting edge wherein the edges are arranged, relative to the deformable member so that both edges and the deformable member, at least in part, substantially abut one another in the absence of any wire gripped by the clamping member.

24. An orthodontic cutter comprising:
at least one flush cutting edge;
an interior recess formed adjacent to the edge; and
a deformable wire clamping member substantially carried in the recess, with a friction fit, the deformable member having first and second free ends wherein each end carries an insertion tab.

* * * * *